United States Patent
Pessin (10) Patent No.: US 7,097,636 B2
(45) Date of Patent: Aug. 29, 2006

(54) NEEDLE PROTECTION DEVICE INTENDED FOR A CARPULE AND INJECTION DEVICE COMPRISING A CARPULE AND THIS PROTECTION DEVICE

(75) Inventor: Olivier Pessin, Grezieu la Varenne (FR)

(73) Assignee: SEDAT, Irigny (FR)

( * ) Notice: Subject to any disclaimer, the term of this patent is extended or adjusted under 35 U.S.C. 154(b) by 0 days.

(21) Appl. No.: 10/995,035

(22) Filed: Nov. 23, 2004

(65) Prior Publication Data

US 2005/0119623 A1    Jun. 2, 2005

(30) Foreign Application Priority Data

Nov. 24, 2003 (FR) .................................. 03 13757

(51) Int. Cl.
    *A61M 5/00*    (2006.01)
(52) U.S. Cl. ...................................... 604/187; 604/232
(58) Field of Classification Search ................ 604/187, 604/192, 197, 198, 110
    See application file for complete search history.

(56) References Cited

U.S. PATENT DOCUMENTS

| | | | | |
|---|---|---|---|---|
| 4,747,831 A * | 5/1988 | Kulli | ........................ | 604/110 |
| 4,828,548 A * | 5/1989 | Walter | ................... | 604/164.08 |
| 4,832,696 A * | 5/1989 | Luther et al. | .......... | 604/164.08 |
| 4,931,040 A * | 6/1990 | Haber et al. | ................ | 604/110 |
| 4,986,819 A * | 1/1991 | Sobel | ......................... | 604/198 |
| 5,112,307 A * | 5/1992 | Haber et al. | ................ | 604/110 |
| 5,261,880 A * | 11/1993 | Streck et al. | ............... | 604/110 |
| 5,267,972 A * | 12/1993 | Anderson | ................... | 604/192 |
| 5,360,410 A | 11/1994 | Wacks et al. | | |
| 5,380,296 A | 1/1995 | Smedley et al. | | |
| 5,891,104 A | 4/1999 | Shonfeld et al. | | |
| 5,891,105 A * | 4/1999 | Mahurkar | .................... | 604/195 |
| 5,989,226 A | 11/1999 | Hymanson | | |
| 6,565,540 B1 * | 5/2003 | Perouse et al. | ............ | 604/192 |
| 6,569,115 B1 * | 5/2003 | Barker et al. | ............... | 604/110 |
| 2002/0068921 A1 | 6/2002 | McWethy et al. | | |
| 2002/0156426 A1 * | 10/2002 | Gagnieux et al. | .......... | 604/197 |
| 2004/0015137 A1 * | 1/2004 | Hohlfelder et al. | ........ | 604/246 |

* cited by examiner

Primary Examiner—Nicholas D. Lucchesi
Assistant Examiner—Laura Bouchelle
(74) Attorney, Agent, or Firm—Sughrue Mion, PLLC (57) ABSTRACT

The auxiliary device (2) for protecting a needle (30) comprises:
  a protector support (20) which delimits a chamber (27) for receiving a reservoir (1) of fluid to be injected, which reservoir is provided with a piston (8) and which support (20) is provided with means (31) for being fixedly joined to the reservoir (1);
  a needle protector (22) which can be moved relative to the support (20) between a retracted position and a deployed position for protecting the needle (30).

The support (20) comprises the needle (30) along the axis of the chamber (27). The joining means (31) comprise hooks (32) which protrude in the chamber (27) and which delimit, around the needle (30), a cage (31) for resiliently latching around the neck (10) of a carpule (1) which forms the reservoir.

10 Claims, 9 Drawing Sheets

NEEDLE PROTECTION DEVICE INTENDED FOR A CARPULE AND INJECTION DEVICE COMPRISING A CARPULE AND THIS PROTECTION DEVICE

TECHNICAL FIELD

The present invention relates to a needle protection device of the type comprising:
- a protector support which delimits a chamber for receiving a reservoir of fluid to be injected, which reservoir is provided with a piston and which support is provided with means for being fixedly joined to the reservoir;
- a needle protector which can be moved relative to the protector support between a retracted position and a deployed position for protecting the needle.

BACKGROUND TO THE INVENTION

A number of medicinal substances are packaged in carpules. A carpule is formed by a generally cylindrical body, one end of which has a narrow neck which is closed by means of a perforatable membrane.

The liquid to be injected is retained in the body of the carpule by means of a sliding piston.

In order to carry out the injection, the carpule is provided with a needle and an activation device. To this end, the carpule is generally placed in an auto-injection device which comprises a body in which the carpule is received. A spring brings about the activation of the piston of the carpule.

Furthermore, it is known to provide injection syringes with needle protection devices which allow the needle to be covered at the end of the injection in order to prevent accidental pricking from the end of the needle when the syringe is manipulated.

The needle protection devices are attached to a syringe body. These devices are generally fixedly joined to the syringe body by the device being resiliently latched on a finger support collar which is provided in the rear portion of the syringe.

Carpules are not provided with profiles of this type at the rear ends thereof, with the result that positioning a needle protection device on a carpule is a complex operation.

The object of the invention is to provide a needle protection device which can be adapted to a carpule.

SUMMARY OF THE INVENTION

To this end, the subject-matter of the invention is a protection device of the type defined above, characterised in that it comprises the needle, which needle is carried by the protector support on the axis of the chamber and has an injection end which protrudes from the chamber and a perforation end which protrudes in the chamber, and in that the joining means comprise hooks which protrude in the chamber and which delimit, around the needle, a cage for resiliently latching around the neck of a carpule which forms the reservoir.

According to other features of this device, taken in isolation or according to all technically possible combinations:
- it comprises a spring which is interposed between the protector support and the needle protector, which spring is initially compressed and can urge the needle protector towards the deployed position thereof;
- the protector support comprises, at the end thereof for introducing the carpule into the chamber, a collar for supporting the spring;
- the needle protector comprises an outer collar which allows the fingers of the practitioner to be supported in order to carry out an injection;
- it comprises a push-button which is initially connected to the protector support or the protector, which push-button delimits a cavity for initially receiving the injection end of the needle and comprises an end for connecting to a moveable piston of the carpule;
- the push-button is integral with the needle protector;
- the push-button is fitted to the protector support; and
- the protector support and the needle protector comprise complementary resilient latching means which can bring about the retention of the needle protector in the deployed position thereof.

The subject-matter of the invention is also an injection device which comprises, on the one hand, a carpule which comprises a tubular body which has, at a distal end, a neck and an injection piston which is mounted so as to be able to slide in the body and, on the other hand, a needle protection device as described above.

BRIEF DESCRIPTION OF DRAWINGS

The invention will be better understood from a reading of the following description, given purely by way of example and with reference to the drawings, in which:

FIGS. 11 to 13 illustrate the injection device in the deployed position, FIG. 11 being a view similar to that of FIG. 8, FIG. 12 being a view sectioned along plane XII—XII indicated in FIG. 11, and FIG. 13 is a view identical to that of FIG. 11, the carpule not being illustrated.

DESCRIPTION OF PREFERRED EMBODIMENTS

Figure 1:
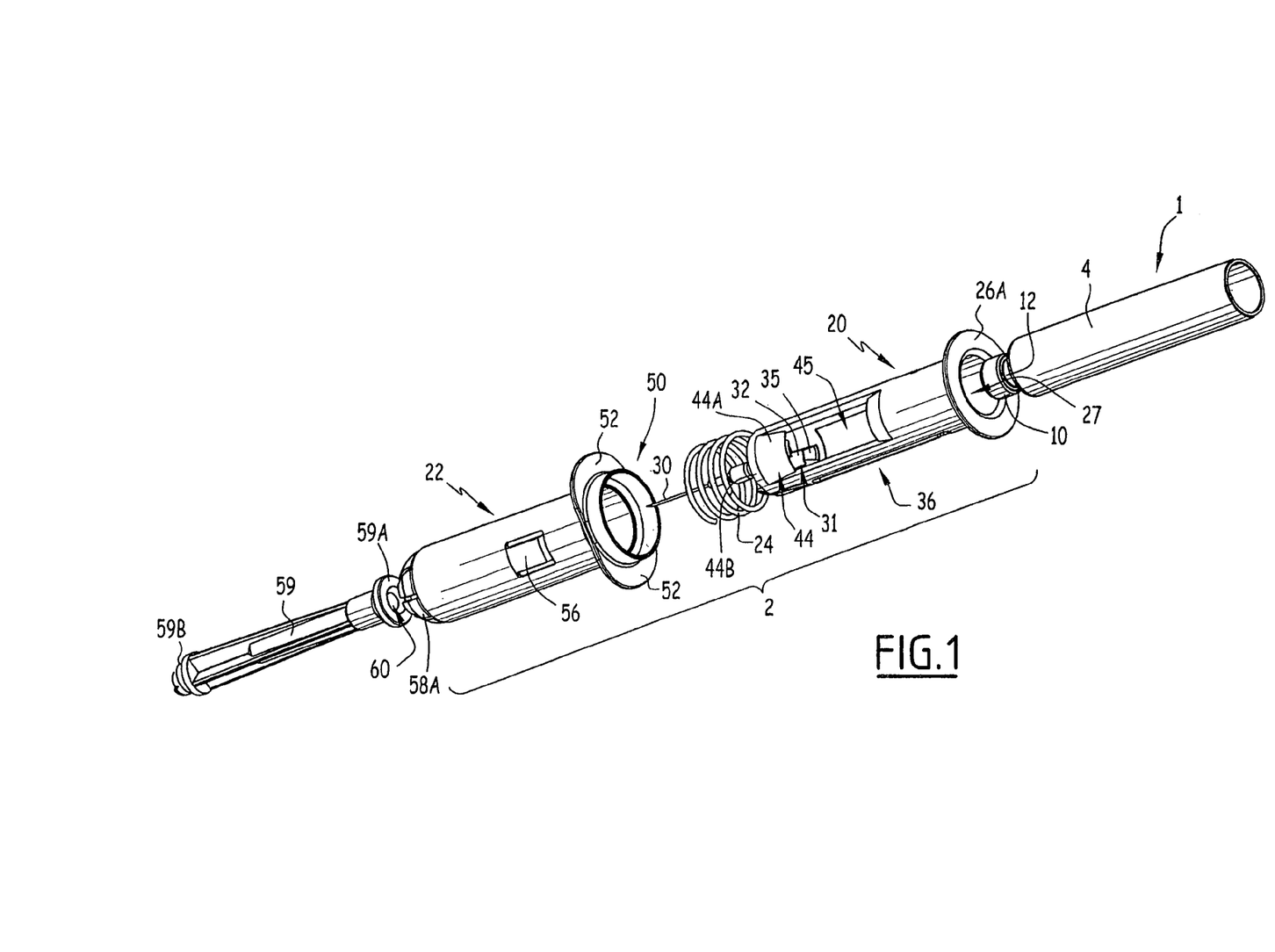
FIG. 1 is an exploded perspective view of an injection device according to the invention before assembly.

FIG. 1 is a perspective view of a carpule 1 and a protection assembly 2. In the following, the terms "proximal" and "rear" are synonymous, as are the terms "distal" and "front".

The carpule 1 is a glass carpule of standard form, intended for a single use. It contains a liquid to be injected into a patient in an intramuscular or subcutaneous manner. To this end, it mainly comprises a body 4 which is in the form of a cylinder generated by revolution and a sliding piston 8 which can be seen in FIG. 6.

The body 4 of the carpule comprises, at the distal portion thereof, a narrow neck 10 which delimits at the rear a circumferential shoulder 12. The neck 10 is closed by means of a perforatable cap 14. The cap 14 is held on the neck by means of a crimped metal hoop.

The body 4 is cylindrical and has a circular cross-section over the main part of the length and at the proximal end thereof and has no external protuberances.

The protection assembly 2, generally having an axis X—X, mainly comprises, as illustrated in FIG. 1:
  a support 20 generally of tubular form;
  a protective sleeve 22 which is arranged coaxially with the support 20 and which has a diameter greater than that of the support 20, and
  a spring 24.

Figure 2:
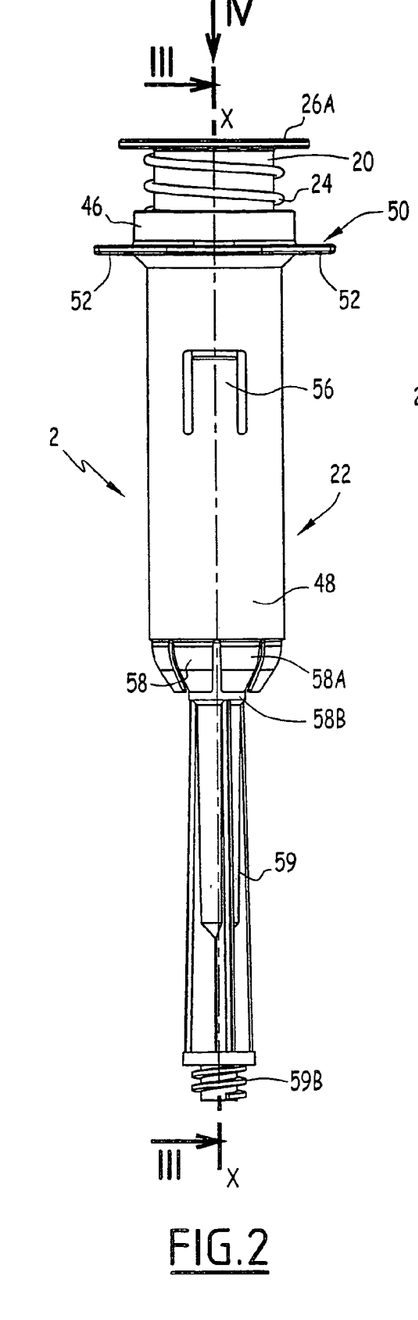
FIG. 2 is a front view of the protection device, which belongs to the injection device of FIG. 1, in the retracted position.

These three elements will be explained successively below, with reference to FIGS. 2 to 4.

The support 20 comprises a main portion 26 which is substantially cylindrical and which delimits a chamber 27 for receiving the carpule 1. This chamber has an inner diameter which is substantially equal to the outer diameter of the body 4 of the carpule. This portion 26 has, at the proximal end thereof, an outer collar 26A which forms a support face for the spring 24.

The support portion 26 is closed, at the distal end thereof, by a transverse wall 28 for supporting the neck of the carpule. The wall 28 is generally in the form of a disc and delimits, at the centre thereof, a passage for an injection needle. The wall 28 is axially extended by a collar 29 for supporting a hollow injection needle 30. The collar 29 protrudes at the outer side of the chamber 27 along the support axis 20. The free end of the collar 29 is constricted on the hollow needle 30 in order to bring about the retention thereof by means of adhesive-bonding or over-moulding.

The needle 30 has an injection end 30A which is arranged at the outer side of the support and an end 30B for perforating the carpule which protrudes at the inner side of the chamber 27 along the axis thereof. In this manner, the end 30B extends behind the wall 28.

Furthermore, the protection device comprises means 31 for fixedly joining the support 20 to the carpule 1. These means 31, which can be seen in particular in FIG. 6, comprise resiliently deformable hooks 32 which can resiliently latch around the neck 10 of the carpule, behind the shoulder 12, with the neck 10 being confined in a cage 31A which is delimited between the hooks and the transverse wall 28.

Figure 6:
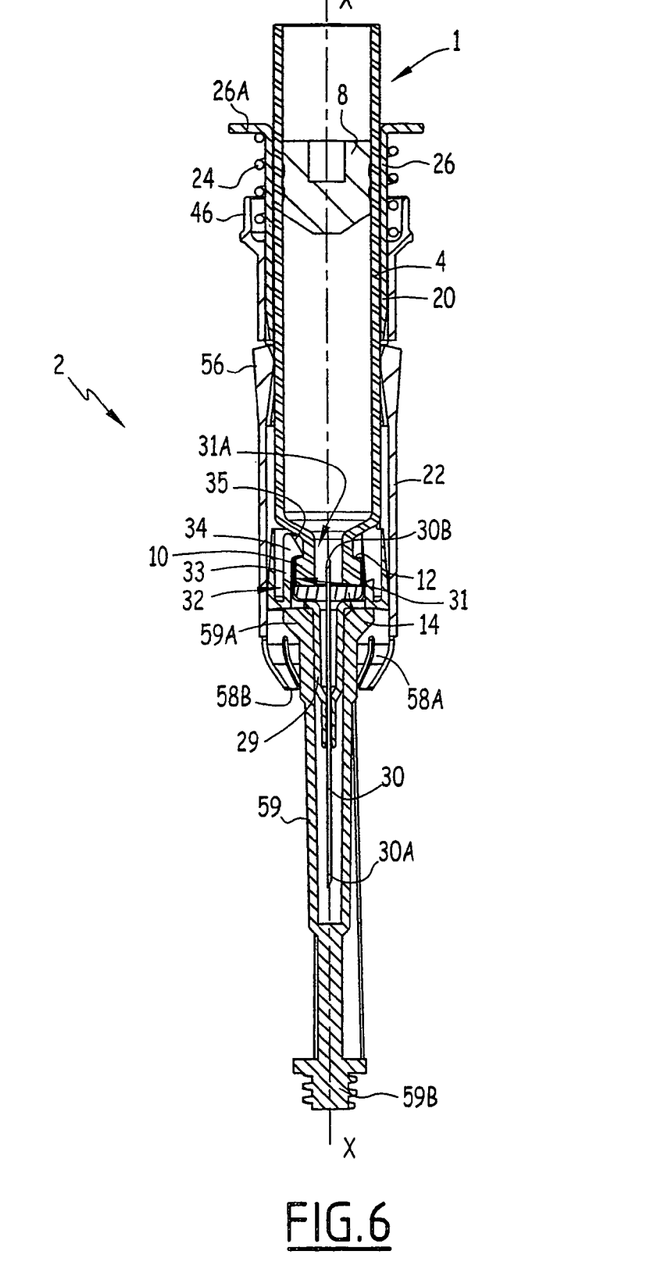
FIG. 6 is a view along the same plane of section as that of FIG. 3 of the injection device after a carpule has been positioned and before the push-button has been positioned.

These hooks are integral with the support 20. There are, for example, two of them and they are distributed about the longitudinal axis of the support. They each have a leg 33 which generally extends parallel with the axis of the needle 30. Each leg 33 is fixedly joined at one end to the wall 28 and has, at the other end thereof, a projection 34 which is directed towards the support axis. This projection 34 can engage behind the shoulder 12 which is delimited by the neck 10 of the carpule.

Advantageously, the projection 34 of each hook has an inclined ramp 35 which is directed towards the proximal end of the support, the ramps 35 converging towards each other in the direction of the needle 30.

Figure 3:
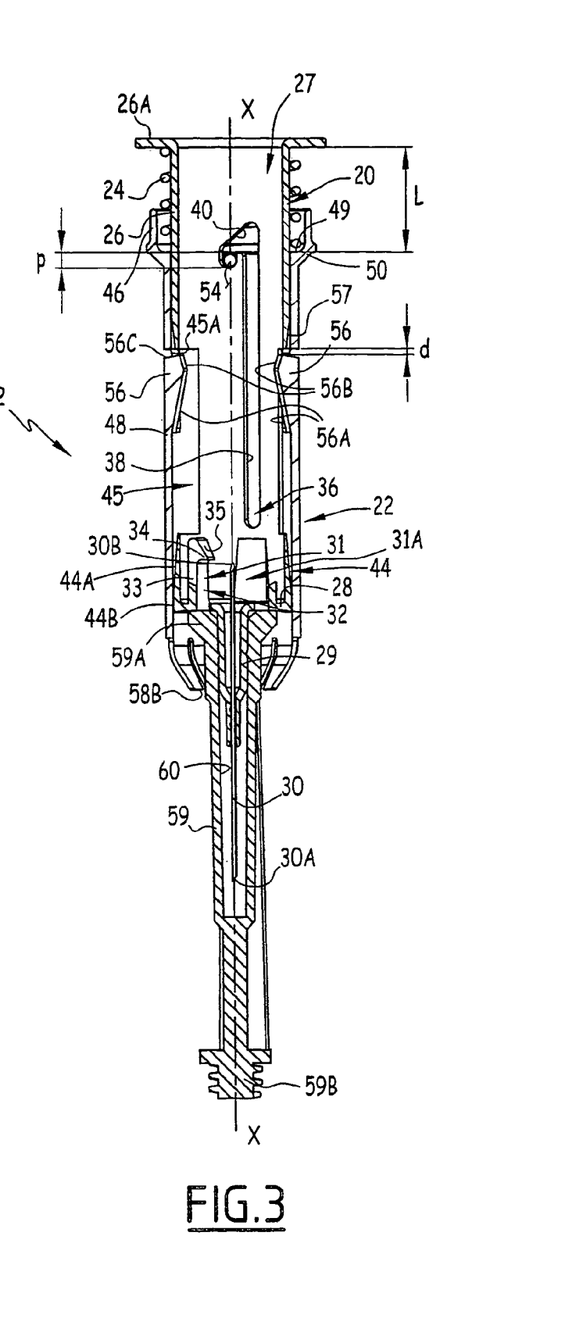
FIG. 3 is a view sectioned along plane III—III which is indicated in FIG. 2.

Two crook-like elongate grooves 36, one of which can be seen in FIG. 3, are provided facing each other in the main portion 26. Each groove is constituted by a first rectilinear portion 38 which extends substantially along the axis X—X of the support 20 over a length which is greater than that of the needle 30, and by a second rectilinear portion 40 which extends in an inclined manner relative to the same axis X—X. The inclined portion 40 opens at the proximal end of the first rectilinear portion 38, forming a V whose point is directed toward the proximal end of the assembly 2.

Figure 5:
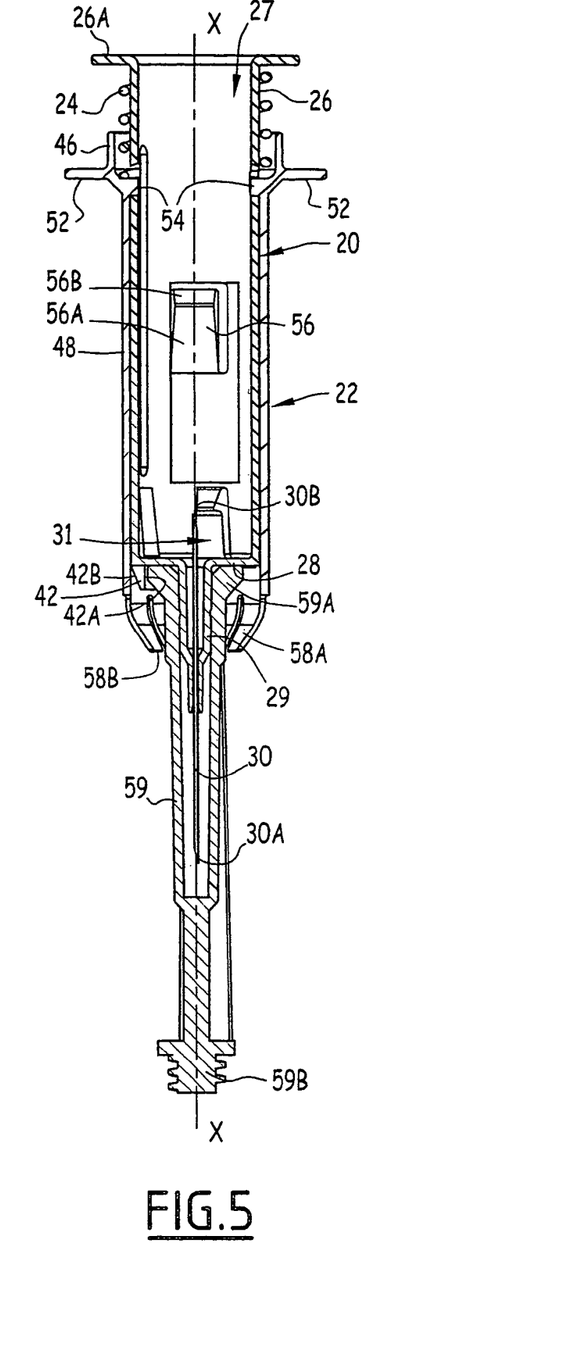
FIG. 5 is a view sectioned along the plane designated V—V in FIG. 4.

The main portion 26 comprises, at the distal end thereof, beyond the transverse wall 28, a first pair of diametrically opposed resilient tongues 42 which are each located in the extension of the grooves 36 (FIG. 5). These tongues 42 have an inner face 42A having a substantially cylindrical form and a substantially frustoconical outer face 42B which widens towards the rear.

The main portion 26 comprises a pair of diametrically opposed outer ramps 44 which are located between the resilient tongues 42 along the circumference of the distal end of this portion. They have an inclined outer surface 44A which is substantially frustoconical and which widens towards the front, and a substantially cylindrical distal surface 44B.

Longitudinal recesses 45 are provided in the main portion 26 (FIG. 3) at the proximal end of these ramps 44. The outer surfaces 44A are thus directed towards the recesses 45.

The protective sleeve 22 has a length which is substantially equal to that of the body 4 of the carpule 1. It is constituted by two cylindrical portions 46 and 48, the proximal portion 46 having a slightly larger diameter than that of the main portion 48. These two portions join together with a radial shoulder 49 being formed for supporting the spring 24.

Figure 4:
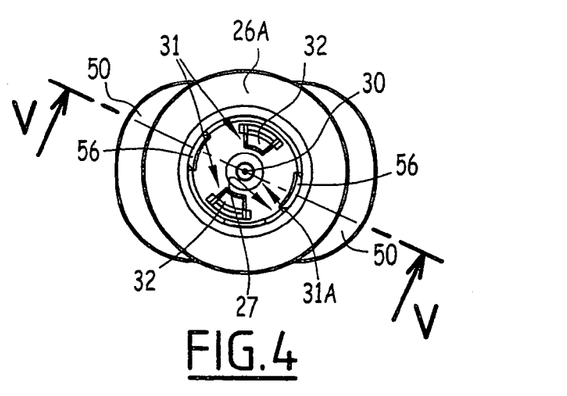
FIG. 4 is a plan view according to arrow IV indicated in FIG. 2.

The sleeve 22 integrally comprises, in the proximal portion thereof, an outer collar 50 in the form of two diametrically opposed lugs 52 (FIG. 4).

Also in the proximal portion thereof, but inside the protective sleeve 22, two diametrically opposed pins 54 are fixedly joined to the sleeve (FIG. 5). These two pins are received and guided in the two grooves 36 of the support 20. The support and the sleeve can thus be moved relative to each other in translation along the common axis thereof and with limited rotation about the same axis when the pins are located in the inclined portions 40. The inclined portions 40 then form pockets for retaining the pins 54, these pockets having a retention depth which is designated p in FIG. 3. This depth is measured along the axis of the protector.

Figure 11:
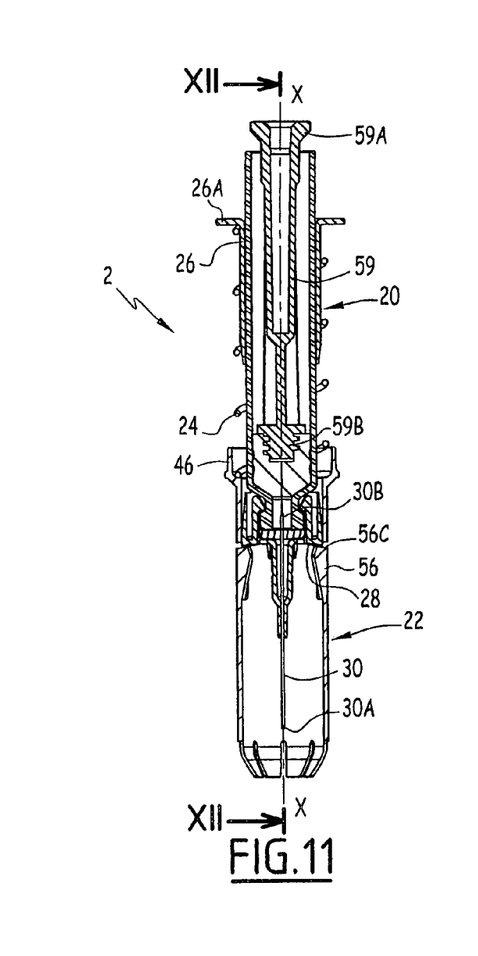
Figure 12:
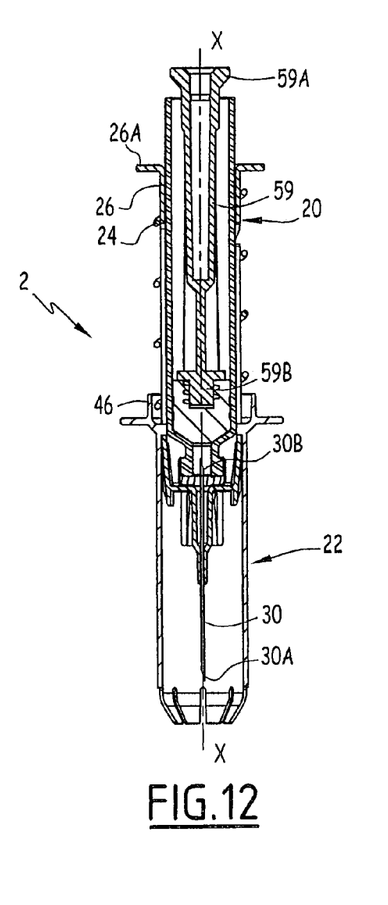
Figure 13:
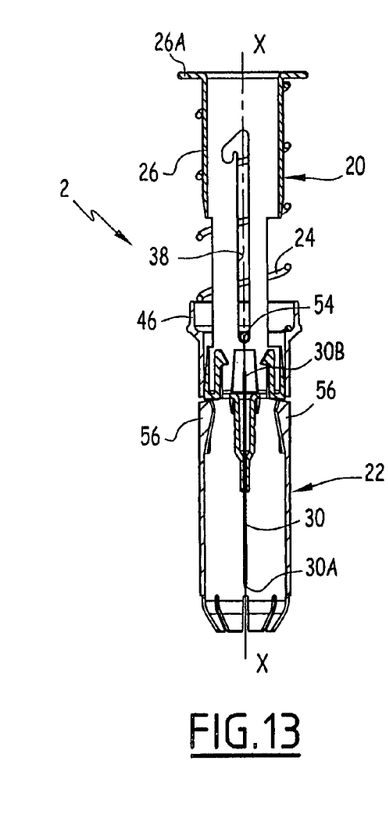

More precisely, the support 20 and the sleeve 22 can be moved between a retracted position of the sleeve, in which the main part of the sleeve covers the main part of the support and the pins 54 are located at the distal end of each of the inclined groove portions 40, as illustrated in FIGS. 2 to 7, and a deployed position of the sleeve, in which the sleeve axially protrudes from the support and the pins are located at the distal end of the rectilinear groove portion 38, as illustrated in FIGS. 11 to 13.

When the carpule 1 is fixed to the assembly 2, these extreme positions correspond, respectively, to an injection configuration in which the needle 30 is released and is intended to be inserted into a patient, and a protection configuration in which this needle is surrounded by the protective sleeve 22.

The proximal portion of the sleeve 22 further comprises, at the inner side, a pair of deformable longitudinal hooks 56 which are diametrically opposed. These hooks are delimited in the sleeve 22 by lateral slots. These hooks are connected to the sleeve at the distal end thereof. Each hook has, at the free proximal end thereof, an inner protuberance.

When no carpule is provided, as illustrated in FIG. 3, the outer surfaces of the hooks 56 extend in a continuation of the sleeve. Conversely, the inner protuberances of these hooks protrude at the inner side of the cylindrical passage which is delimited by the sleeve 22. Each protuberance has a substantially frustoconical front face 56A which moves away, towards the front, from the axis of the sleeve 22. These front faces 56A are thus directed towards the front end of the protector.

Each front face 56A is adapted in order to co-operate with an inclined surface 44A formed by the ramps 44 of the support.

Furthermore, each inner protuberance has a rear inclined face 56B which is directed towards the rear end of the protector and in particular towards the two lugs 52. These surfaces 56B are generally frustoconical and diverge away from each other in the direction of the rear end of the protector.

The support 20 comprises frustoconical ramps 57 which are arranged at the rear of the recesses 45. These ramps are inclined towards the recesses 45 and are adapted to co-operate with the inclined rear faces 56B.

Each hook 56 has, at the free end thereof, an inclined transverse face 56C which forms a stop.

When no carpule is provided, as illustrated in FIG. 3, the face 56C of each hook extends immediately opposite the corresponding end of the recess 45 which defines a support face 45A for the face 56C. The distance d which separates the end face 56C from the edge of the recess is less than the depth p of the retention pocket formed by the inclined groove portion 40 in which the pin 54 is received.

When the sleeve is in the retracted position, the hooks 56 extend at the inner side of the recesses 45 which are provided in the support 20. When the sleeve is in the deployed position, as illustrated in FIG. 11, the end faces 56C of the hooks 56 are in axial abutment against the transverse wall 28, the hooks and tongues thus forming a rigid locking assembly in the deployed position.

The sleeve 22 is further provided, at the distal end thereof, with a frustoconical crown 58 having a diameter which becomes progressively smaller towards the free end thereof.

In this embodiment, the frustoconical crown 58 is formed by a crown of resiliently deformable tongues 58A whose distal edges form a substantially circular opening 58B.

The protective sleeve 22 is initially extended, at the free distal end thereof, by a push-button 59 which allows the piston of the carpule to be activated. This push-button 59 is constituted by a rod which has, at the rear end thereof, a collar 59A for supporting the thumb and, at the front or distal end thereof, a thread 59B which can co-operate with a complementary thread provided on the exposed face of the piston 8.

The diameter of the opening 58B, when the tongues are in the rest position, is less than the diameter of the collar 59A of the push-button.

The push-button 59 is hollow and delimits a housing 60 which opens axially at the centre of the collar 59A for supporting the thumb. The housing 60 initially receives the end 30A of the needle 30, as illustrated in FIGS. 3 and 6. In this manner, the push-button 59 initially forms a protection cap for the needle.

The shape of the housing 60, in the vicinity of the opening thereof, complements that of the collar 29 in such a manner that, as illustrated in FIG. 3, the collar 29 fits exactly in the housing 60. In order to retain the push-button 59 on the support 20, a rib is provided in the inner wall which delimits the housing 20, whilst a complementary collar protrudes on the collar 29 in order to bring about resilient latching. In this position, the collar 59A of the push-button is pressed against the wall 28 and extends between this wall and the tongues 58A of the protective sleeve.

The spring 24 is a helical spring which is arranged between the protective sleeve 22 and the protector support 20. More precisely, the spring is accommodated between the collar 26A of the support and the shoulder 49 of the sleeve 22. When the sleeve is in the retracted position, the spring 24 is in a compressed state, thus having decompression energy which is connected with the rigidity of the spring and the difference between the length of the spring in the rest state and its length, designated L in FIGS. 2 to 7, in the compressed state. That is to say that the spring 24 has a supplementary compression force threshold which corresponds to the minimum force necessary to further compress the spring from the initial compressed state thereof of FIGS. 2 to 7. The rigidity of the spring and/or the initial compression length L are selected in such a manner that this force threshold is greater than the pushing force which is needed to displace the piston 8 of the carpule 1 over the entire injection path thereof. More precisely, the force of the spring in the locked state is greater than the sum of the injection force, that is to say, for evacuating the liquid out of the needle 30 and the debonding and sliding forces of the piston 8 at the inner side of the body 4 of the carpule.

The injection device according to the invention operates as follows:

The protection device 2 is assembled in its retracted configuration, that is to say, that of FIGS. 2 to 7. To this end, the protective sleeve 22 is fitted around the support 20 from the distal end of the support, with the spring 24 being arranged therebetween. More precisely, the sleeve is displaced axially towards the rear relative to the support, with the hooks 56 being deformed radially outwards by means of an appropriate tool so that they axially reach the front portion of the longitudinal recesses 45. Then, with the sleeve still being displaced towards the rear, the pins 54 are pressed against the outer surfaces 42B of the tongues 42 until the pins are received in the groove portions 38. The displacement of the protector 22 towards the rear then continues until the pins 54 are received in the inclined groove portions 40, the support and the protector being caused to pivot relative to each other. The protector is thus once more in a retracted position. Finally, the tool is removed.

In this position, as illustrated in FIG. 3, the inner protuberances of the hooks 56 protrude at the inner side of the passage for receiving the carpule in such a manner that the rear transverse surface 56C extends immediately in front of the corresponding edge of the recess 45.

The end face forms a stop which is capable of co-operating with the edge of the recesses 45 in order to prevent a movement of the protective sleeve 22 towards the rear end of the support 20. The hooks 56 are then in a locking position.

As will subsequently be explained, in so far as the retention of the spring which brings about the displacement of the protective sleeve is released by the protector being displaced towards the rear, any risk of accidental unlocking of the protective sleeve during transport of the protective device is prevented since the protective sleeve is locked in the release direction thereof independently of the means for retaining the spring, as long as no carpule is introduced in the protector support.

The carpule 1 is pre-filled with a liquid to be injected into a patient.

The carpule is inserted inside the assembly 2 in order to form the injection device, as illustrated in FIG. 6. More precisely, the body 4 of the carpule is displaced substantially axially at the inner side of the support 20. When the body 4 of the carpule engages in the support 20, as illustrated in FIG. 6, the neck 20 engages between the projections 34 of the hooks 32, being supported firstly on the inclined ramps 35. When the neck 10 is pressed, the free ends of the hooks 32 move apart which allows the neck to engage between the hooks. When the projections 34 have moved past the shoulder 12 of the neck, the hooks straighten resiliently, which brings about the engagement of the projections 34 behind the shoulder 12 and the confinement of the neck 10 in the cage 31A defined between the projections 34 of the hooks and the transverse wall 28.

The carpule is therefore axially immobilised relative to the support 20.

When the neck engages between the hooks, the cap 14 is perforated by the hollow needle 30 from the end 30B thereof.

In this manner, the liquid which is contained in the carpule is in contact with the hollow needle and can flow through the needle.

When the practitioner is ready to carry out the injection of the liquid contained in the carpule, he detaches the push-button 59 by pulling it axially forwards.

When it engages, the tongues 58A resiliently deform in order to allow the collar 59A to pass. The tongues then resume their original position after the collar 59A has passed so that the push-button can no longer be repositioned after an initial retraction, the inclined tongues 58A preventing the passage of the collar 59A as far as the space delimited between the support 20 and the protective sleeve 22.

Figure 7:
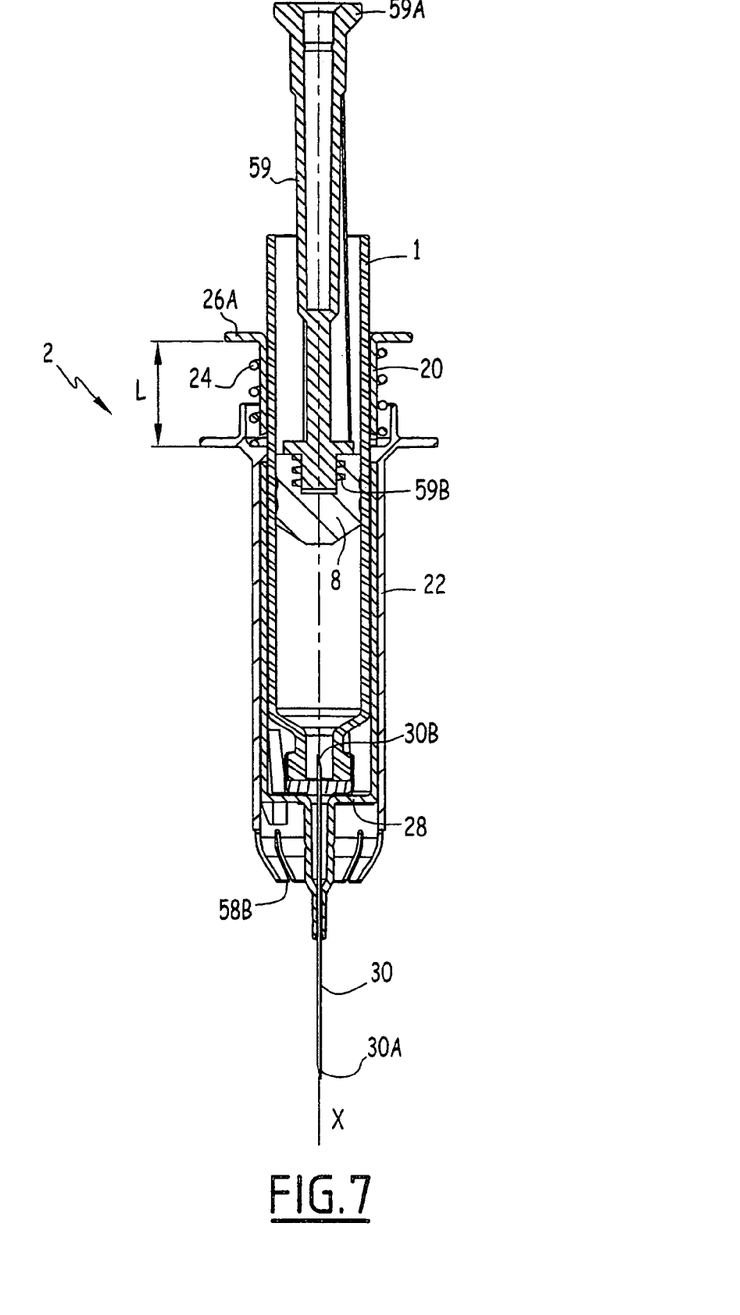
FIG. 7 is a view similar to that of FIG. 5, the injection device being in use.

After the push-button 59 has been detached, it is screwed from the threaded end 59B thereof into the piston 8. It then extends as illustrated in FIG. 7. In this configuration, the injection end 30A of the needle is exposed.

The practitioner then inserts the needle 30 into a patient. He injects the liquid contained in the carpule by applying a pushing force to the push-button 59 which is connected to the piston 8, his index finger and middle finger remaining in contact with the faces of the lugs 52 that are directed towards the needle. During the injection, no movement occurs between the protector support 20 and the protective sleeve 22, the spring 24 remaining compressed with a length L, as illustrated in FIG. 7.

The injection is continued until the push-button 59 and the piston 8 reach the end of the injection stroke.

Figure 8:
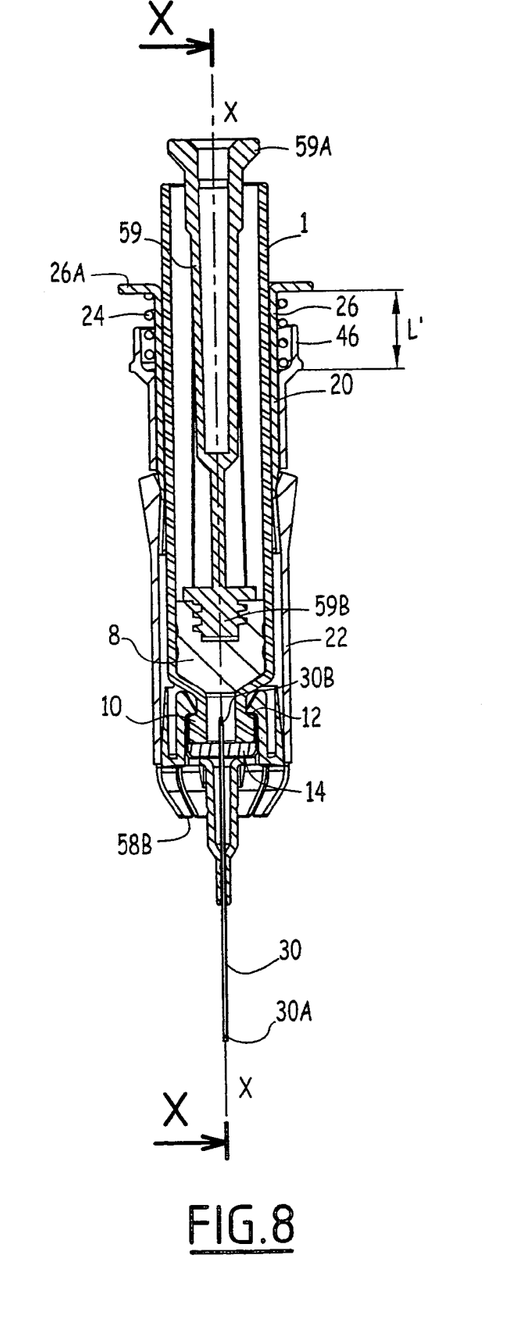
FIG. 8 is a view along the same plane of section as that of FIG. 5 of the injection device at the end of an injection operation.
Figure 9:
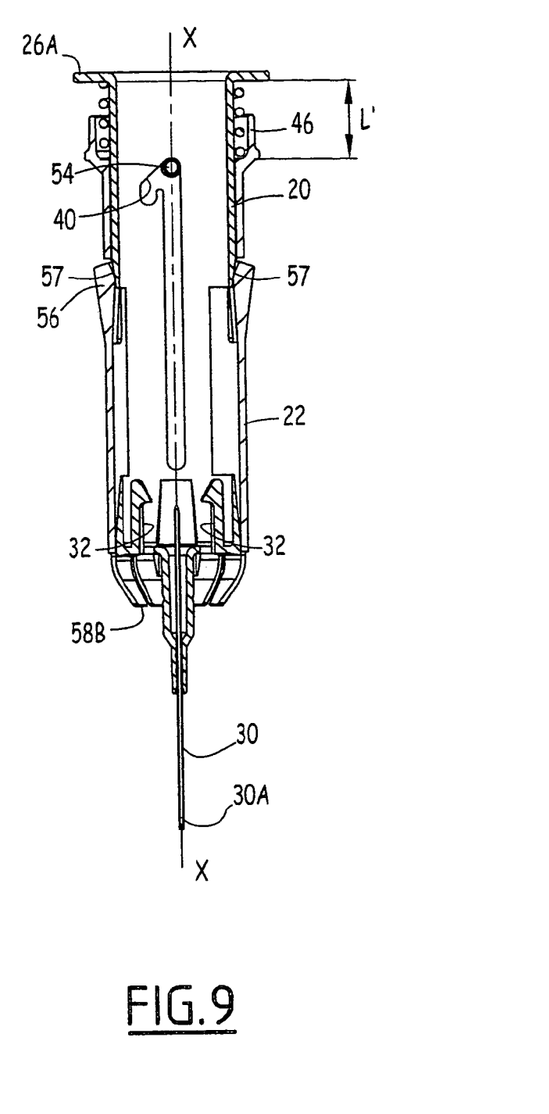
FIG. 9 is a view identical to that of FIG. 8, the carpule of the injection device not being illustrated.
Figure 10:
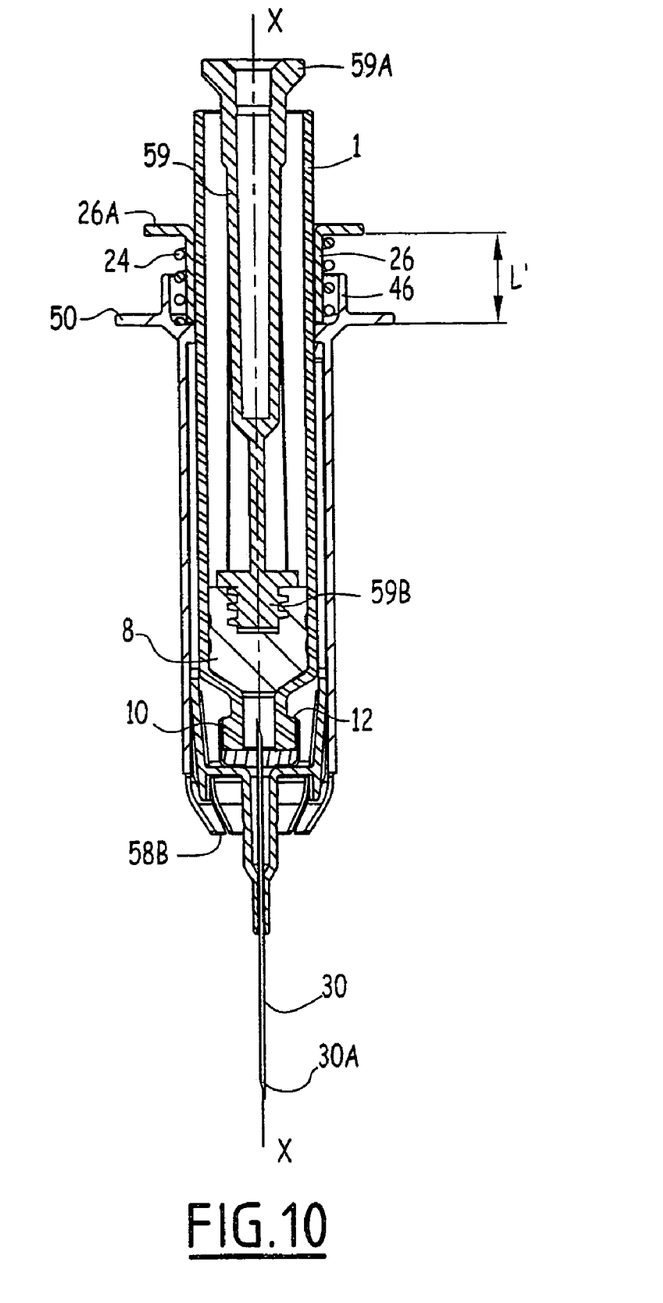
FIG. 10 is a view sectioned along plane X—X indicated in FIG. 8.

The practitioner then removes the needle from the patient. In order to release the protection assembly 2, the practitioner applies additional pressure to the push-button 59 and the piston 8. This pressure must be greater than the predetermined force produced by the spring 24 in the locked state so that this spring is further compressed and changes from the length L thereof to a shorter length L', as illustrated in FIGS. 8 to 10. To that end, taking the stationary carpule as a support, the protective sleeve 22 is axially displaced towards the proximal end of the support 20. The practitioner carries out this movement by applying a corresponding pressure to the lugs 52 of the collar 50 of the sleeve 22 using his index and middle fingers. This pressure brings about, combined with the translation movement, the rotation of the protective sleeve 22 about the carpule support 20, the pins 54 being guided by the inclined groove portions 40. This rotation movement continues until the pins reach the proximal end of this groove portion 40, that is to say, the proximal end of the longitudinal groove portion 38, as can be seen in FIG. 9. The device 2 is then in the unlocking position of the spring 24.

The movement of the needle protector towards the rear end of the support in the direction of release of the spring is made possible by the co-operation of the inclined rear faces 56B of the protuberances of the hooks and the ramps 57. When the protector moves, an increased deformation of the hooks towards the outer side is brought about, as illustrated in FIG. 8. In this manner, the hooks move apart from each other in order to pass above the outer surface of the protective sleeve beyond the recesses 45.

The practitioner then releases the pressure which he had been applying to the collar 50 until then, which allows the spring 24 to relax into a rest state. The studs 54 move in translation at the inner side of the longitudinal groove portion 38, as far as the distal end thereof, as illustrated in FIG. 13. The translation movement of the protective sleeve 22 relative to the support 20 can be controlled by the practitioner if he progressively releases the finger hold which he applies to the collar 50. When the studs 54 have arrived at the distal end of the groove 36 (FIG. 13), the protector is in the deployed position thereof.

Furthermore, when the protective sleeve moves in translation relative to the support 20, the hooks 56 follow the longitudinal recesses 45 of the support, until they slide along the distal ramps 44 of the support, by means of co-operation of the complementary surfaces 56A and 44A thereof.

When the protector is in the deployed position, the hooks 56 are held by means of co-operation of the surfaces 56C and 28B, so that the protective sleeve 22 cannot be brought into its initial position. In the same manner, the sleeve 22 cannot be readily pulled from the support 20 since the pins 54 abut against the distal base of the longitudinal groove portion 38 (FIG. 13).

The injection device according to the invention is thus simple to use whilst allowing the practitioner to control the movement for covering the needle by the protective sleeve.

The number of components which constitute the illustrated protection assembly 2 is reduced to three.

The device according to the invention can be adapted to different types of carpule, both in terms of shape and volume. This device therefore has the advantage of not changing the general shape of the carpules which are used and consequently requires no modification of the industrial methods for filling these carpules.

Various variants of the device according to the invention are possible; the pins 54 and/or the collar 50 of the protective sleeve 22 can be attached to the sleeve 22 and not be produced as one piece therewith.

Figure 14:
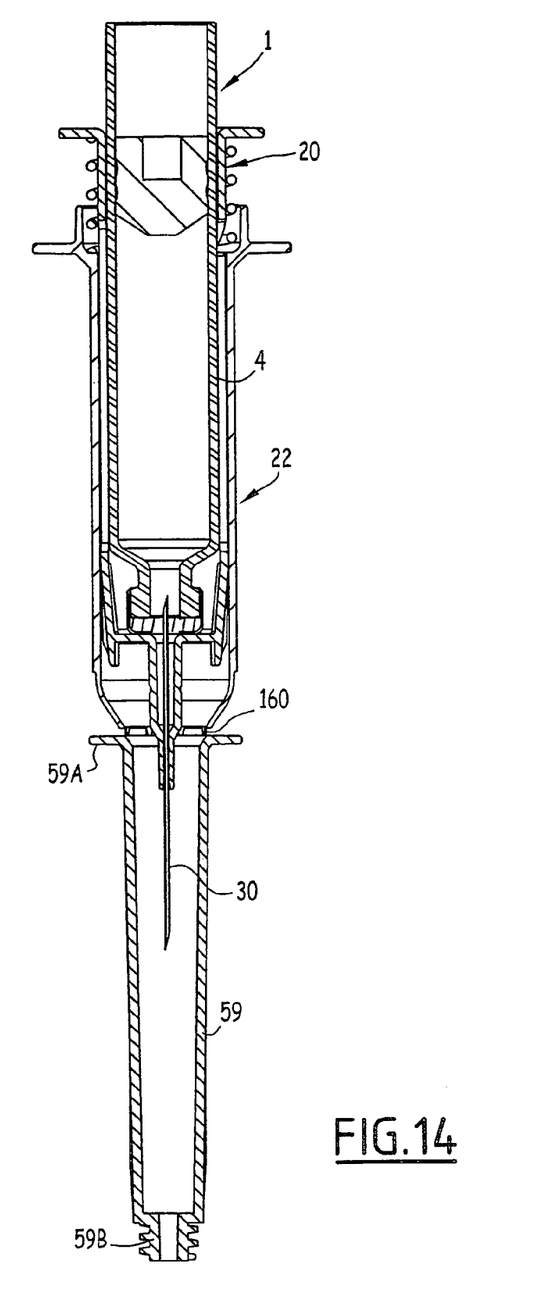
FIG. 14 is a view identical to that of FIG. 6 of a production variant of a device according to the invention.

As illustrated by the variant in FIG. 14, the push-button 59 is integral with the protective sleeve 22 and is connected to the protective sleeve by means of breakable connecting pieces and in particular breakable webs 160.

The invention claimed is:

1. An auxiliary needle protection device comprising:
 a protector support which delimits a chamber extending along an axis for receiving a carpule containing fluid to be injected, having a neck at an extremity, closed by a cap, and provided at an opposed extremity with a piston, the support comprising an end for introducing the carpule into the chamber along the axis of the chamber;
 a needle carried by the protector support in the axis of the chamber and having an injection end which protrudes from the chamber and a perforation end which protrudes into the chamber;

joining means provided on the support for fixedly joining the carpule to the support, the joining means comprising hooks which protrude in the chamber and which delimit, around the needle, a cage for resiliently latching around the neck of the carpule;

whereby upon axial insertion of the carpule into the chamber through the introduction end, the hooks engage the neck of the carpule to axially immobilise the carpule relative to the support, and the cap of the carpule is perforated by the perforation end of the needle;

a collar provided on the support at the end for introducing the carpule into the chamber;

a needle protector which can be moved relative to the protector support between a retracted position and a deployed position for protecting the needle;

a spring which is interposed between the collar of the protector support and the needle protector, which spring is initially compressed and can urge the needle protector towards the deployed position thereof.

2. Needle protection device according to claim 1, wherein the needle protector comprises an outer collar which allows the fingers of the practitioner to be supported in order to carry out an injection.

3. Needle protection device according to claim 1, wherein it comprises a push-button which is initially connected to the protector support or the protector, which push-button delimits a cavity for initially receiving the injection end of the needle and comprises an end for connecting to a moveable piston of the carpule.

4. Needle protection device according to claim 2, wherein it comprises a push-button which is initially connected to the protector support or the protector, which push-button delimits a cavity for initially receiving the injection end of the needle and comprises an end for connecting to a moveable piston of the carpule.

5. Needle protection device according to claim 3, wherein the push-button is integral with the needle protector.

6. Needle protection device according to claim 4, wherein the push-button is integral with the needle protector.

7. Device according to claim 3, wherein the push-button is fitted to the protector support.

8. Device according to claim 4, wherein the push-button is fitted to the protector support.

9. Device according to claim 1, wherein the protector support and the needle protector comprise complementary resilient latching means which can bring about the retention of the needle protector in the deployed position thereof.

10. Injection device comprising, on the one hand, a carpule which comprises a tubular body which has a narrow neck which delimits a shoulder and which is provided with a perforatable closing cap and an injection piston which is mounted so as to be able to slide in the body and, on the other hand, a needle protection device according to claim 1.

* * * * *